(12) United States Patent
Eberhard (10) Patent No.: US 9,937,291 B2
(45) Date of Patent: *Apr. 10, 2018

(54) PISTON PUMP

(71) Applicant: B. BRAUN MELSUNGEN AG, Melsungen (DE)

(72) Inventor: Dietmar Eberhard, Kenzingen (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/427,616

(22) Filed: Feb. 8, 2017

(65) Prior Publication Data

US 2017/0145992 A1  May 25, 2017

Related U.S. Application Data

(62) Division of application No. 14/384,987, filed as application No. PCT/EP2013/054766 on Mar. 8, 2013.

(30) Foreign Application Priority Data

Mar. 19, 2012 (DE) ........................ 10 2012 102 274

(51) Int. Cl.
F04B 7/00 (2006.01)
A61M 5/168 (2006.01)
(Continued)

(52) U.S. Cl.
CPC .... *A61M 5/16881* (2013.01); *A61M 5/14216* (2013.01); *A61M 5/16831* (2013.01);
(Continued)

(58) Field of Classification Search
CPC ...... F04B 7/007; F04B 7/0011; F04B 7/0023; F04B 7/0026; F04B 13/00; F04B 39/1066;
(Continued)

(56) References Cited

U.S. PATENT DOCUMENTS

| | | |
|---|---|---|
| 1,164,831 A | 12/1915 | McDermott |
| 1,774,662 A | 9/1930 | Parks |

(Continued)

FOREIGN PATENT DOCUMENTS

| | | |
|---|---|---|
| CN | 2614275 Y | 5/2004 |
| CN | 101429932 A | 5/2009 |

(Continued)

OTHER PUBLICATIONS

U.S. Notice of Allowance for U.S. Appl. No. 14/384,967, dated May 15, 2017, 18 pages.

(Continued)

*Primary Examiner* — Nathan Zollinger
(74) *Attorney, Agent, or Firm* — RatnerPrestia (57) ABSTRACT

A piston pump is described for pumping a fluid. The pump includes at least one cylinder having a piston movable inside the cylinder along the longitudinal axis of the cylinder by a drive, each cylinder having at an end face a mounting flange having at least one cylinder opening, and a chamber having a volume that changes when the associated piston is moved in the cylinder. The piston pump has an inlet port for supplying and an outlet port for draining the fluid. A rotatable valve plate is arranged on the other side of the mounting flange. The mounting flange has at least one passage in the region of the inlet port and the outlet port, respectively, through which the fluid can flow between the inlet port and/or the outlet port and the other side of the mounting flange. The valve plate has fluid-transporting means by which, upon rotation of the valve plate at least one cylinder opening can be connected to a passage of the inlet and/or the outlet port.

13 Claims, 10 Drawing Sheets

(51) Int. Cl.

| | |
|---|---|
| *A61M 5/36* | (2006.01) |
| *F04B 13/00* | (2006.01) |
| *F04B 39/10* | (2006.01) |
| *F04B 19/22* | (2006.01) |
| *F04B 51/00* | (2006.01) |
| *F04B 53/14* | (2006.01) |
| *F04B 53/16* | (2006.01) |
| *A61M 5/142* | (2006.01) |

(52) U.S. Cl.
CPC .......... *A61M 5/365* (2013.01); *F04B 7/0007* (2013.01); *F04B 7/0023* (2013.01); *F04B 13/00* (2013.01); *F04B 19/22* (2013.01); *F04B 39/1066* (2013.01); *F04B 51/00* (2013.01); *F04B 53/14* (2013.01); *F04B 53/16* (2013.01); *A61M 5/14212* (2013.01); *A61M 2005/16863* (2013.01); *A61M 2205/332* (2013.01); *A61M 2205/3375* (2013.01)

(58) Field of Classification Search
CPC ........ F04B 7/0007; F04B 19/22; F04B 51/00; F04B 53/14; F04B 53/16; A61M 5/16831; A61M 5/365; A61M 5/16881; A61M 5/14212; A61M 5/14216; A61M 2005/16863; A61M 2205/332; A61M 2205/3375
USPC .......................................... 417/519; 137/876
See application file for complete search history.

(56) References Cited

U.S. PATENT DOCUMENTS

| | | |
|---|---|---|
| 4,854,836 A | 8/1989 | Borsanyi |
| 5,811,659 A * | 9/1998 | Giebler ................. A61M 5/365 604/65 |
| 6,171,253 B1 | 1/2001 | Bullister et al. |
| 7,887,308 B2 | 2/2011 | Navarro |
| 9,427,517 B2 | 8/2016 | Eberhard |
| 2005/0178206 A1 | 8/2005 | Malmstrom et al. |
| 2006/0278001 A1 | 12/2006 | Kaneko et al. |
| 2007/0196224 A1 | 8/2007 | Lenhart |
| 2008/0294040 A1 | 11/2008 | Mohiuddin et al. |
| 2011/0021990 A1 | 1/2011 | Navarro et al. |
| 2011/0206545 A1 | 8/2011 | Junod et al. |

FOREIGN PATENT DOCUMENTS

| | | |
|---|---|---|
| DE | 3838689 C1 | 6/1990 |
| DE | 20317579 U1 | 2/2004 |
| DE | 102005058080 A1 | 6/2007 |
| DE | 102005058100 B3 | 8/2007 |
| JP | 1973000644 | 1/1973 |
| JP | 2002130589 A | 5/2002 |
| JP | 2011017331 A | 1/2011 |
| RU | 2324070 C2 | 5/2008 |
| SU | 1011893 A1 | 4/1983 |

OTHER PUBLICATIONS

German Search Report for German Application No. 10 2012 102 274.7, dated May 19, 2017 with translation, 12 pages.
International Search Report for International Application No. PCT/EP2013/054766, dated May 24, 2013, 3 pages.
German Search Report for German Application No. DE 2012 102 274.7, dated Nov. 13, 2012, 4 pages.
English translation of Japanese Exam Report for JP 2015-500834 dated Aug. 4, 2015, 3 pages.
Japanese Office Action dated Dec. 15, 2015 for Japanese Application No. 2015-500834, with English translation, 5 pages.
CN Office Action with Search Report for CN 201380015418.3, with translation, dated Jan. 4, 2016, 14 pages.
Decision to Grant for Russian Application No. 2014142060/06(068088), dated Jan. 24, 2017 with translation, 17 pages.

* cited by examiner

PISTON PUMP

CROSS REFERENCE TO RELATED APPLICATIONS

This application is a divisional application of U.S. application Ser. No. 14/384,967 filed Sep. 12, 2014, which is a U.S. national phase application of PCT International Application No. PCT/EP2013/054766 filed Mar. 8, 2013, which claims priority to German Patent Application No. DE 10 2012 102 274.7 filed Mar. 19, 2012, the contents of each application being incorporated by reference herein.

FIELD OF THE INVENTION

The invention relates to a piston pump for pumping a fluid, comprising at least one cylinder having a piston which is movable inside the cylinder along the longitudinal axis of the cylinder with a drive, each cylinder having at an end face a mounting flange having at least one cylinder opening, and a chamber having a volume that changes when the associated piston is moved in the cylinder is formed on the cylinder-side, between each piston and a mounting flange. Furthermore the piston pump has an inlet port for supplying, and an outlet port for draining the fluid.

BACKGROUND

Such a piston pump is particularly suited for use in medical infusion/dialysis technology. Predominantly tube pumps and injection pumps are currently in use. Tube pumps which work according to the peristaltic principle are used above all when larger quantities of fluid are to be administered. A provision of these quantities of fluid occurs for example with an infusion bag. In the case of syringe pumps the delivery volume through the injection body is limited and includes generally not more than 50 ml, wherein some models even allow a liquid supply of up to 100 ml.

DESCRIPTION OF THE RELATED ART

Tube pumps according to the peristaltic principle are very widespread and are also ambulatorily used for artificial nutrition for example. Because of its pump principle, their delivery accuracy is worse than that of injection pumps.

Periodically operating piston pumps by contrast comprise a high delivery accuracy, as with syringe pumps, and can suck in and pump out liquids from an exchangeable storage tank, as with peristaltic pumps.

A piston pump for medical infusion technology is known from U.S. Pat. No. 7,887,308 B2 for example. This pump possesses, in a first exemplary embodiment, a cylindrical housing which comprises inlet and outlet ports lying radially opposite to each other. Inside the housing a piston moves bidirectionally with a rotor attached to it, such that it moves axially along the longitudinal axis of the housing and at the same time also rotates around this longitudinal axis. With this movement, alternating channels within the piston are respectively connected to an inlet and outlet port, whereby a fluid can be conveyed in a measured way. In another exemplary embodiment of the pump, two coaxial pistons are provided which both move within a movable housing along the longitudinal axis of this housing and thus form chambers with variable volumes within the housing. A valve plate is arranged between the two pistons, into which are introduced inlet and outlet ports that lie opposite each other. The valve plate is bidirectionally moved with a rotor attached to it, as in the first exemplary embodiment, whereby the housing moves backwards and forwards along the longitudinal axis of the pistons. At the same time channels within the valve plate are alternately uncovered by the rotation of the valve plate around the longitudinal axis and the cylinder chambers are alternately connected with the inlet and outlet ports, whereby the pump can continuously pump. Since the inlet and outlet ports are attached to the reciprocating valve plate, the connecting tubes however move with the pump motion, which leads to significant movement of the accompanying pump parts and can be unfavorable. In particular this functionality requires much space, which among other things impedes a compact construction of the pump.

With a periodically working piston pump it is therefore possible to achieve a high delivery accuracy even with large delivery volumes. However it is often desirable here to form such a piston pump and other components very compactly, in order to be able to integrate them into a housing which is a small as possible. This is the case for example when one is dealing with medical single-use articles and/or infusion technology in the field of home care, wherein pumps for exchangeable infusion containers should be easy to connect for the patient, unskilled family members or the caregiver. It has proved advantageous to accommodate the entire pump with its additional components in a type of cassette. Included among these additional components are in particular sensor systems for the detection of occlusions and air bubbles.

The detection of an occlusion takes place usually by an indirect measurement of the internal pressure in a tube which serves for supplying a fluid. If an occlusion exists, the internal pressure of the tube downstream from the pump for example increases, which can be indirectly measured. For this purpose, the tube's round cross-section deforms elliptically with a biasing force for example and the tube's internal pressure to be determined increases or reduces this biasing force which then may be determined with a force sensor. DE 38 38 689 C1 discloses exemplarily such a method for pressure measurement and occlusion detection.

Furthermore such a method has the disadvantage that the deformation of the tube leads generally to a creep process lasting hours. This creep releases tension in the tube cross-section which leads to a continuous changing of the measured force. The undesired change in force caused by the creeping is of a similar order of magnitude to the desired measuring effect with variation of the tube inner pressure and therefore hinders the reliable recognition of an occlusion. Special elastomers such as for example silicone comprise a significantly reduced creep behavior and are therefore predestined as the tube segment for the occlusion sensor. A combination of silicon with non-silicone materials is however very costly because process-safe bonded joints are not possible.

Furthermore air bubble detection in medical infusion sets as well as in dialysis applications is prescribed as a necessity. Usually the recognition occurs via ultrasonic transmitters and receivers which are coupled sonically on both sides to the tube piece to be observed. However it is not metrologically possible to distinguish an air bubble which lies between the ultrasonic components and a fluid-filled tube, from an air-filled piece of tube. Therefore usually the tube piece is manually squeezed by special supports between the two ultrasonic components and correspondingly deformed, so that there is a high chance that an air bubble is avoided.

When inserting a tube set into a pump, according to the current state of the art, the tube segments responsible for the individual sensors must be inserted by hand in special supports, which can be problematic not only in the field of home care. Relevant state of the art is also known from documents US 2008/0 294 040 A1, US 2011/0 021 990 A1 and U.S. Pat. No. 4,854,836 A.

SUMMARY OF THE INVENTION

An object of the invention is therefore to provide a piston pump which permits a compact construction and simple handling both for the pumping function and for additional components such as occlusion and ultrasound sensors.

The piston pump according to aspects of the invention serves to pump a fluid and includes at least one cylinder having a piston which is movable along the longitudinal axis of the cylinder with a drive within the cylinder, wherein each cylinder comprises at an end face a mounting flange having at least one cylinder opening and forms on the cylinder-side, between each piston and a mounting flange, a chamber with variable volume when the associated piston is moved in the cylinder. Furthermore the piston pump has an inlet port for supplying, and an outlet port for draining the fluid.

According to aspects of the invention a rotatable valve plate is arranged on the side of a mounting flange, which side faces away from a cylinder, which valve plate bears on the respective mounting flange. In the sense of the invention this means that for example a cylindrically shaped valve plate having a main or top surface bears on the mounting flange. Thereby the axis of rotation of the valve plate runs preferably parallel to the direction of motion of the piston, but also deviations from parallelism are covered by the invention, such that also the axis of rotation of the valve plate may run only in the direction of motion. The deviation from parallelism may for example be in the order of 1-20°, but is not limited to these values.

The inlet port and/or outlet port is attached to at least one mounting flange, wherein a mounting flange has at least one passage in the region of an inlet port and an outlet port respectively, through which passage the fluid can flow between the inlet port and/or the outlet port and the other side of the mounting flange. For the valve function, the valve plate has fluid-transporting means by which, upon rotation of the valve plate between two angular positions, in each of the two angular positions at least one cylinder opening can be connected to a passage of an inlet and/or outlet port.

The inlet and outlet ports are thus immobile and independent of the rotary motion of the valve plate. In this way space can be saved with respect to other pump concepts having movable ports. Furthermore the assembly of the piston pump is clearly simpler, and connections from ports to tubes for example are not compromised by the movement of the ports. Thereby the rotary motion of the valve plate is coupled to the reciprocating motion of the pistons of the cylinders, such that the valve function is dependent on piston position.

In one exemplary embodiment of the invention, upon rotation of the valve plate to at least a third position, the fluid-transporting means do not connect a cylinder opening with a passage of an inlet and/or outlet port. In such an angular position, the cylinders or the inlet and/or outlet ports can thus be completely blocked by the valve plate.

Preferably each inlet port and/or outlet port runs in the direction of the at least one cylinder. In addition it has proven to be beneficial that each inlet port and/or outlet port runs parallel to the at least one cylinder, but here also deviations from parallelism are covered by the invention. This deviation may again be in the order of 1-20°, but is not limited to these values. Thus also the axis of rotation of the valve plate may run parallel or at least in the direction of the cylinder axis of the at least one cylinder. Through both means a particularly compact construction of the piston pump, either individually or in combination, can be achieved.

The piston pump can be executed as a single-piston pump, wherein both an individual cylinder and also the inlet and outlet port are located at a common mounting flange. In a further exemplary embodiment of the invention, the piston pump is executed as a multi-piston pump, with which an uninterrupted delivery may be achieved. In addition for example two mounting flanges are provided, between which the valve plate is located, A cylinder having at least one cylinder opening is attached to both mounting flanges respectively, while the inlet and outlet ports are located together at one of the two mounting flanges. In another embodiment of such a multi-piston pump, one of the inlet or outlet ports respectively is attached to each mounting flange. Thus at each mounting flange there are located a cylinder and one of the ports respectively.

The fluid-transporting means may be executed in various ways, in order to realize a connection between cylinder openings and passages to the ports. For example the fluid-transporting means may include at least one cavity which is recessed into a surface of the valve plate, said surface facing a mounting flange having inlet and/or outlet port, wherein the cavity is configured such that, by rotating the valve plate it can be made to coincide simultaneously with a cylinder opening and a passage of an inlet and/or outlet port respectively. Such a fluid-transporting means serves to transport fluid on the flange side to a side of the valve plate and is suitably formed by a channel recessed into the valve plate.

The fluid-transporting means may however also include at least one cavity which also is recessed into a surface of the valve plate facing a mounting flange having inlet and/or outlet port, but furthermore comprises a passage channel which extends out from this cavity through the valve plate, The cavity and the associated passage channel are in that case configured such that by rotating the valve plate they can be made to coincide simultaneously with a cylinder opening and the passage of an opposite-lying inlet and/or outlet port respectively. It is therefore a fluid-transporting means which enables a transport of fluid through the valve plate.

Both variants of the fluid-transporting means may be used selectively or in combination, wherein the choice depends essentially on the selected embodiment of the piston pump. For example in the case of a single-piston pump having inlet and outlet port on the side of the cylinder, fluid transport through the valve plate is not required, such that simple cavities in a side of the valve plate would be sufficient as fluid-transporting means, in order to fulfill the valve function. But as soon as cylinders and/or inlet and outlet ports are distributed on two mounting flanges which are arranged lying opposite on the two sides of the valve plate, fluid-transporting means having a passage channel are required, in order to allow a fluid transport through the valve plate.

Optionally an occlusion sensor may be integrated into an inlet port and/or outlet port of the piston pump respectively, which occlusion sensor cannot be non-destructively disassembled. For example in addition at least one recess may be provided in the inlet and/or outlet port, which is tightly covered by a sensor component composed of a pressure sensitive material. Thereby the material of the inlet and/or outlet port is harder than that of the sensor component, and the piston pump comprises a force sensor with which pressure-induced changes of the sensor component in the region of the respective recess can be measured.

The invention thus can make use of the operating principle of a pressure membrane, but does not use this, in a separate element, rather integrates a corresponding sensor component into a port of a hard material, through which a fluid is delivered anyway. Thereby the occlusion sensor's mechanical sensor component to be integrated rests on the principle of the measurement of pressure in the fluid and is realized with an elastic material which behaves physically analogously to a pressure membrane. The port forms a hard component insensitive to pressure which does not deform under the occurring pressure changes. Due to the occurring deformations of the sensor component as soft component, the internal pressure in the port can on the other hand be determined.

The occlusion sensor may be integrated directly into a hard port so as to save space, which permits a very compact design. The port may be an inlet and/or outlet port which conducts the fluid to a pump or from the same to a patient. In this way the sensor can recognize occlusions ahead of and/or behind a pump. If the associated port is suitably positioned such that it can be compactly accommodated with a pump in a housing, then the occlusion sensor at this port does not require much more space.

The sensor component is thereby preferably an integral and non-removable part of the inlet and/or outlet port such that it also does not have to be installed or even aligned during commissioning of the apparatus. This facilitates the handling of the apparatus and avoids setup errors and thus also measurement errors.

Preferably the force sensor is in contact in the region of the recess with the surface of the sensor component, wherein the force sensor comprises for example a plunger which is in direct contact in the region of the recess with the surface of the sensor component. In this way a change in the expansion of the sensor component in this region can be measured.

Furthermore, for this purpose, the sensor component is composed of an elastomer wherein in particular it can be a silicon or a thermoelastic elastomer. In this way the physical properties of this special elastomer can be advantageously used, which in particular comprises a low creep behavior. A material-fit connection of silicone and non-silicone materials is however not required since appropriate methods, such as for example injection molding methods, can be used for a sealed connection between port and sensor component. In this way the port and the sensor component may be manufactured in a two-component process. Alternatively the connection between port and sensor component may be manufactured with other connection techniques wherein for example plug-in, click, screw or adhesive joints are possible.

In one exemplary embodiment of the occlusion sensor, the sensor component is a tube which surrounds the port with form-locking fit such that it tightly covers the recess from the outside. In another exemplary embodiment, the tube is attached with form-locking fit inside the port such that the sensor component covers a corresponding recess from inside. The port and the sensor component have for this purpose a similar or the same cross-section. For example a tube having a round cross-section may be introduced with form-locking fit into a round port, or may enclose the same. The sensor component does not have to be tubular however, rather it may have any form which is appropriate for a covering of a recess.

Also however it can be advantageous when the sensor component has an elliptical cross-section, wherein a flat side of the sensor component is arranged in the region of the recess. This can be the case for the inner-lying as well as outer-lying sensor components, wherein the cross-section of the port must be correspondingly adjusted. With this form of soft component, the sensor component already has the elliptical deformation necessary for the internal pressure measurement, such that undesired creep behaviors with thermoplastic elastomers can be prevented already to the greatest possible extent.

The elliptical cross-section may for example be achieved by means wherein a tube having originally circular cross-section is suitably deformed before it is assembled to an inlet or outlet port. The deformation is then not brought about through the assembly, but rather there occurs a pre-deformation of the tube to the desired elliptical cross-section in order to prevent undesired creep behavior.

In another exemplary embodiment of the occlusion sensor the sensor component is a specially shaped measurement membrane having a cross-section comprising at least two opposite-lying membrane sides which each are kinked inwards, while a membrane top side which connects the two membrane sides to each other is formed straight and is arranged in the region of the recess. The force sensor thus lies on a straight surface of the measurement membrane, which is no longer changed by the internal stress, such that a linear force characteristic results.

Further optionally, an ultrasound sensor may be integrated into an inlet port and/or outlet port respectively, for the detection of air bubbles in the respective port, which ultrasound sensor cannot be non-destructively disassembled. In one exemplary embodiment of the invention, the ultrasound sensor is executed such that a tube is inserted with form-locking fit into the inlet and/or outlet port, through which fluid is supplied to the inlet port or through which fluid is discharged from the outlet port. Thereby surfaces for the coupling and decoupling of ultrasound are provided in the region of the tube at two sides of the relevant inlet and/or outlet port. These surfaces for the coupling and decoupling of ultrasound may be executed flat, however they can also comprise differently formed surfaces suited to the form of the ultrasonic sensors.

The inlet and/or outlet port is preferably formed such that these surfaces lie in a plane. Furthermore it may be practical for the inlet and/or outlet port to comprise a recess in order to prevent a possible short circuit path of the ultrasound path past the tube piece to be examined. In one exemplary embodiment of the invention this recess lies opposite to the surfaces for the coupling and decoupling of ultrasound, however the recess may be arbitrarily arranged. Also a plurality of recesses are possible for this purpose.

Possible areas of application of the pump according to aspects of the invention are (not exclusively): medical single-use articles of infusion or dialysis systems, or devices having single-use articles for the individual dosage of drugs such as in the pharmacy field. The described arrangement may be integrated into a medical infusion set and replaces the peristaltic segment necessary for the delivery. Mechanical apparatuses may be integrated into this piston pump in addition to the pure pumping function, wherein said mechanical apparatuses form the mechanical part of the required fluid sensors such as for example occlusion or air bubble detection, and constitute a simple mechanical interface to the external electronic sensor components. Thus by the implementation with a sensor component in a port, the pressure measuring segment which is important for the occlusion sensor can also be replaced. With the optional interface to an ultrasound sensor which can recognize potential air bubbles, another prerequisite for a compact cassette system for the pump-and-sensor unit is achieved.

The mechanical sensor components thereby do not have to be deployed as independent components in the pump module through costly mounting or assembly techniques, rather they can form integral and non-removable components of the pump. To this end, intelligent arrangements and a mechanical design have been found, which take into account economical manufacturing techniques and in particular multi-component injection molding techniques. The pump itself may be realized as a periodically operating piston pump, in order to join the advantages of the high delivery accuracy and the ability to deliver from one supply bag.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1A:
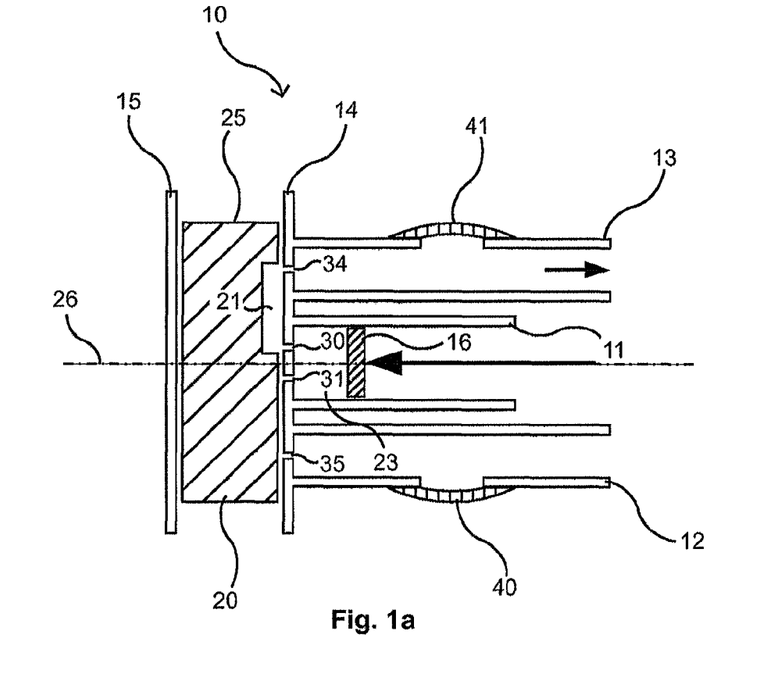
FIG. 1a shows a schematic representation of the functional principle of a first exemplary embodiment of a piston pump as a single-piston pump during the ejection process.
Figure 1B:
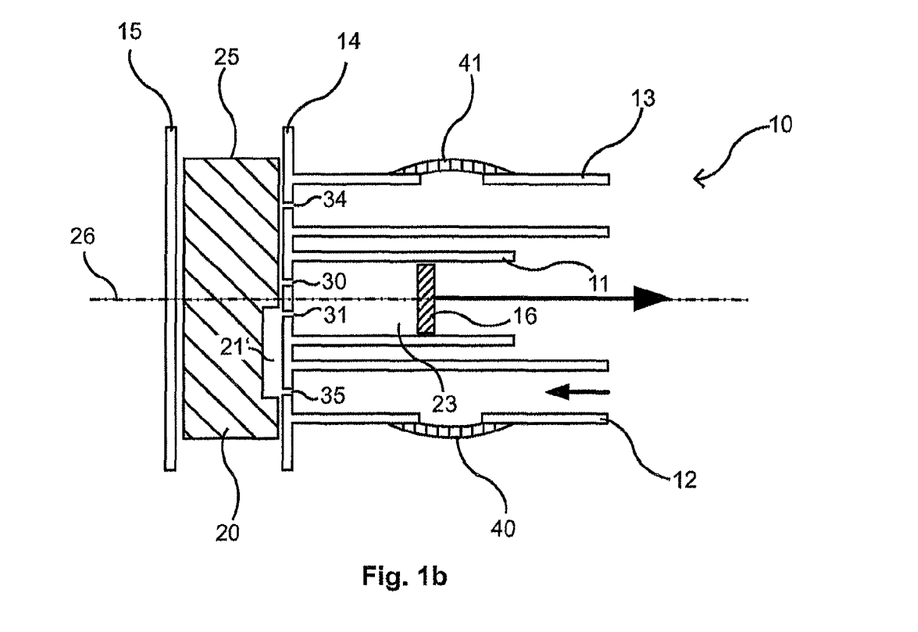
FIG. 1b shows a piston pump according to FIG. 1a during the suction process.

FIG. 1a and FIG. 1b respectively show in a schematic representation an exemplary embodiment of the piston pump according to aspects of the invention in an embodiment as a single-piston pump. FIG. 1a shows the single-piston pump during the ejection process, while FIG. 1b shows the suction process. The movement of a piston 16 and a corresponding fluid to be supplied is indicated for the sucking and the ejection with a respective arrow.

Thereby the schematic representation of FIGS. 1a and 1b do not illustrate any straight section through the piston pump, rather shows only the main path of a fluid during the pumping process. Depicted cylinders, ports and openings are thus not necessarily sectioned through a plane, rather they can also lie in different planes. The same applies to the illustrations of FIGS. 2a, 2b, 3a and 3b. An exemplary embodiment of cylinders, ports and openings in offset planes is for example apparent from the view of FIGS. 4a and 4b.

In the case of the single-piston pump 10 according to FIGS. 1a and 1b, a first flange 14 having a cylinder 11 is provided, into which a piston 16 is movably introduced. Such a flange 14 may also be described as a mounting flange, since it not only surrounds the periphery of the cylinder 11 at the end face, but also further components can be attached to this mounting flange. In particular an inlet port 12 and an outlet port 13 are attached to the flange 14. The cylinder 11 preferably lies between the inlet and outlet port 12, 13, and the longitudinal axes of the cylinder 11 and the inlet and outlet port 12, 13 run essentially parallel to each other. With a movement of the piston 16 inside the cylinder 11 which is caused by a drive (not shown), a chamber 23 having variable volume is formed on the cylinder-side, between the flange 14 and the piston 16. In the region of the end face of the cylinder 11, at least one cylinder opening is provided in the flange 14, through which fluid can flow between the cylinder 11 and the other side of the flange 14 when the piston 16 is moved.

In the embodiments shown in the figures two respective cylinder openings 30 and 31 are provided for each cylinder 11. Furthermore a respective passage 34, 35 is provided in each port 12, 13 in the flange 14, through which fluid also can flow between the respective port and the other side of the flange 14.

The changing-over of the sucking and ejection functions of the pump 10 is realized via a valve plate 20 that rotates backwards and forwards. Thereby the valve plate 20 rotates around the axis of rotation 26 between at least two angular positions, wherein it can be advantageous if the axis of rotation 26 of the valve plate 20 coincides with the cylinder axis and thus with the direction of motion of the piston 16, such as is the case in the figures. However this is not a constraint of the invention.

The valve plate 20 borders on its opposite-lying side on a further flange which is indicated with 15. In addition the valve plate 20 bears on both flanges 14,15 and comprises fluid-transporting means with which a fluid to be pumped is movable via the valve plate between cylinders and ports. The fluid-transporting means are preferably at least one cavity 21, 21' which is recessed into the surface of the valve plate 20 and hence changes its position upon rotation of the valve plate 20. This at least one cavity performs the valve function, wherein a cavity may be realized through circular, curved or straight recessed channels in the surface of the valve plate 20, for example. A sealing medium on the edges of the cavity preferably ensures that the fluid cannot leave the channel geometry. For this purpose, sealing lips may for example be used, or the surfaces of the valve plate 20 form a sealed surface with a special material.

Instead of cavities 21, 21' in the surface of the valve plate 20, other forms of channels may be provided for the transport of a fluid via or through the valve plate 20. For example they may even be holes through the valve plate, which pass under the surface of the valve plate on the flange side and which then realize the transport of a fluid through the valve plate with their two openings on this side.

In the ejection process of FIG. 1a, a cavity 21 in the upper region coincides with a cylinder opening 30 and also with a passage 34 in the outlet port 13. The cylinder opening 31 and the passage 35 in the inlet port 12 are by contrast covered and thus blocked by the valve plate 20. In the event of a movement of the piston 16 in the direction of the arrow, previously sucked-in fluid is thus pushed from the chamber 23 through the cylinder opening 30 into the cavity 21 and from there pushed through the passage 34 into the outlet port 13. From there the fluid may for example be supplied via a tube to some further components or to a patient.

After the ejection the valve plate 20 rotates to a second angular position which can be seen in FIG. 1b and whereby now a cavity 21' in the lower region coincides with the cylinder opening 30 and simultaneously also with the passage 35 in the inlet port 12. When the piston 16 moves at the same time in the direction of the arrow, then fluid is sucked in through the inlet port 12 from a storage tank (not shown). Thereby the fluid is sucked from the inlet port 12 through the passage 35 into the cavity 21' and from there through the cylinder opening 30 into the chamber 23 in the cylinder 11.

During ejection the connection from the cylinder 11 to the outlet port 13 is activated by a certain angular region of the valve plate 20, while another angular region connects the inlet port 12 with the cylinder 11 during sucking. The valve control occurs therefore through a reciprocating motion of one piston which is dependent on piston stroke. As is seen in FIGS. 1a and 1b, a cavity 21, 21' of the valve plate 20 coincides alternately with another of the two cylinder openings 30, 31. Also however, it may be provided that only one cylinder opening is provided, wherein the cavities 21, 21' and said cylinder opening are suitably formed and positioned, in order to coincide in both angular positions of the valve plate 20.

In the depicted exemplary embodiment of FIGS. 1a and 1b, two cavities 21 and 21' are provided which however do not have to be symmetrically arranged on the valve plate, also rather they may be positioned at an angle of less than 180° offset with respect to each other. For example the valve function may be achieved through two cavities which are arranged 90° offset with respect to each other. In this way the valve plate needs only to be rotated by this angle in order to change between the two positions. According to the arrangement of the ports 12, 13 and of the cylinder 11 on the flange 14, this angle can be further reduced or increased.

The valve function may also however be achieved through a single cavity which is reciprocated between the two described angular positions. In this case the cavities 21 and 21' would be identical. Then the valve plate 20 would possibly have to be rotated by a larger angular region, according to the arrangement of the ports 12, 13 and of the cylinder 11, in order to bring the cavity into the two required positions.

Further variants with several cylinders may be derived from the single-cylinder solution, which are shown exemplarily in FIGS. 2a to 3b. Corresponding to FIGS. 2a and 2b for example, a second cylinder 11' with piston 16' is integrated into the flange 15. Both pistons 16, 16' always move in the same horizontal direction, whereby one piston per position of the valve plate 20 takes over the sucking function, and the other takes over the ejection.

Figure 2A:
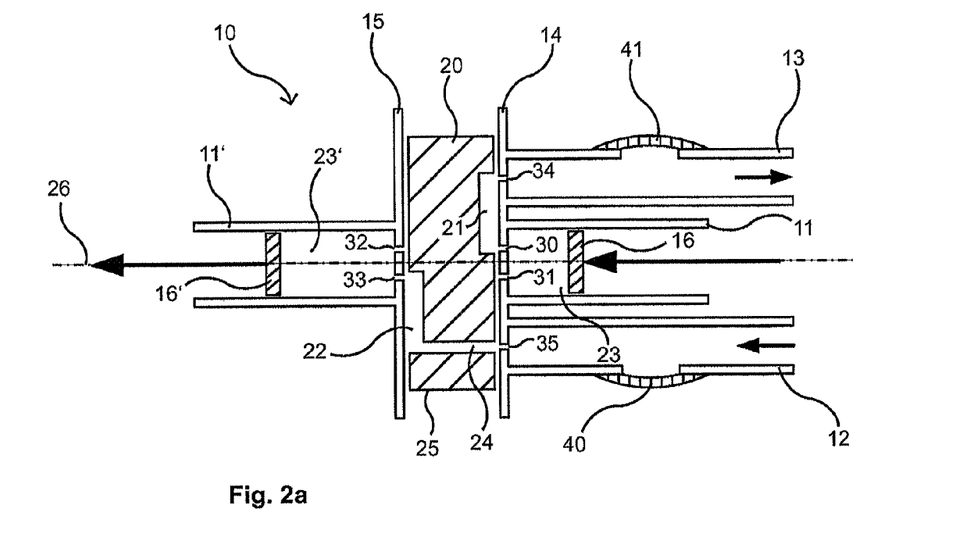
FIG. 2a shows a schematic representation of the functional principle of a second exemplary embodiment of a piston pump as a multi-piston pump having inlet and outlet port on one side, in a first piston position.

Upon ejection by the piston 16, previously sucked-in fluid is pushed through the cylinder opening 30 into the cavity 21 and from there through the passage 34 into the outlet port 13. At the same time fluid is sucked from the inlet port 12 through the passage 35 and into a channel 24 inside the valve plate 20, with the movement of the other piston 16'. This channel 24 runs through the valve plate 20 and connects both sides to each other. The channel 24 opens out into a further cavity 22 on the other side of the valve plate 20, which is formed and arranged such that it coincides with the cylinder opening 33 in the cylinder 11'. In this way the fluid can flow from the inlet port 12 into the chamber 23' of the cylinder 11'.

Figure 2B:
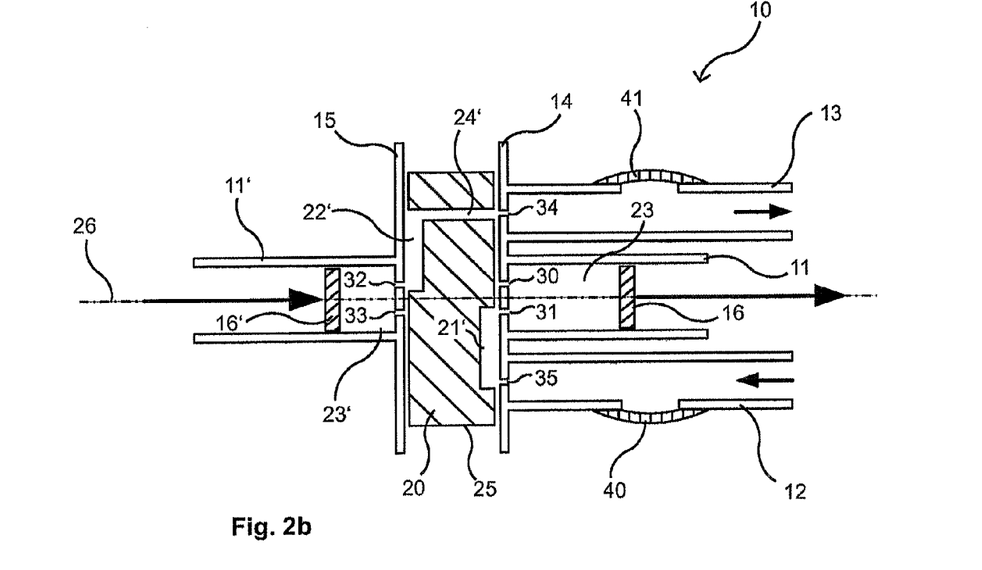
FIG. 2b shows a multi-piston pump according to FIG. 2a in a schematic cross-section.

If the pistons 16, 16' now move in the other direction, as shown in FIG. 2b, the valve plate 20 is located at a second angular position. Now fluid is sucked from the inlet port 12 through the passage 35, the cavity 21' and the cylinder opening 31 into the chamber 23, while the fluid sucked previously into the chamber 23' is pushed through the passage 32, the cavity 22', the channel 24' and the passage 34 on the other side of the valve plate 20 into the outlet port 13. By repeating this procedure, the pumping is nearly uninterrupted.

Different types of cavities 21 and 22 are thus provided in the valve plate, wherein a first cavity type 21 serves to transport fluid on one side of the valve plate between a cylinder and a port. This type of cavity is formed by suitable channels in the surface of the valve plate 20 and represents a cavity for the transport of fluid on the flange side. The second cavity type 22 by contrast serves for the transport of a fluid from one side of the valve plate to the other such that this cavity 22 is always connected to a channel 24 through the valve plate and represents a cavity for transport of fluid through the valve plate. The recessed channel within the surface of the valve plate 20 is typically formed differently as compared to the first cavity type 21.

Thereby one or both cavity types can be provided respectively on one side of the valve plate according to the embodiment of the piston pump. In the embodiment of FIGS. 2a and 2b, a single cavity on each side of the valve plate may be used again for both angular positions, since each side requires only one cavity type.

Figure 3A:
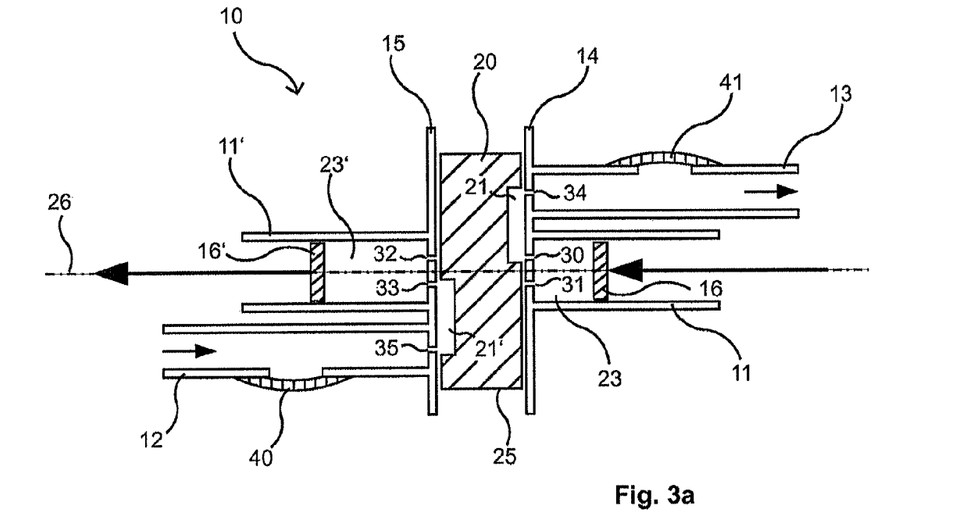
FIG. 3a shows a schematic representation of the functional principle of a third exemplary embodiment of a piston pump as a multi-piston pump having inlet and outlet ports on two sides, in a first piston position.
Figure 3B:
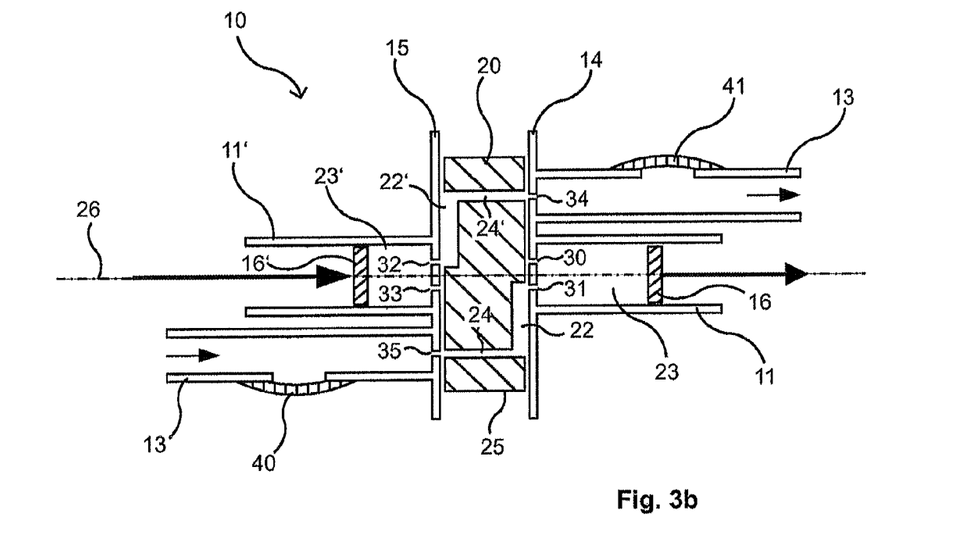
FIG. 3b shows a multi-piston pump according to FIG. 3a in a second piston position.

FIGS. 3a and 3b show a further embodiment of a piston pump 10, whereby a second cylinder 11' and the inlet port 12 are attached to the flange 15. The outlet port 13 and the first cylinder 11 are located on the other flange 14. For this arrangement the valve plate 20 must be modified again with the various types of cavities in order to be able to deliver fluid between the two sides in the various angular positions of the valve plate 20. Thereby a respective cavity of each type is provided on each side of the valve plate such that the right side comprises one cavity 21 without passage channel and one cavity 22 with passage channel 24. The left side of the valve plate comprises also a cavity 21' without passage channel and a second cavity 22' with passage channel 24'. In this embodiment, cavities on one side of the valve plate therefore cannot be used for two angular positions, since different cavity types are required in the angular positions.

In the piston position of FIG. 3a, the fluid is pushed from the chamber 23 through the cylinder opening 30 into the cavity 21 and from there through the passage 34 into the outlet port 13. At the same time fluid is sucked from the inlet port 12 through the passage 35 into the cavity 21' and from there through the cylinder opening 33 into the chamber 23'. In this angular position of the valve plate 20 there is therefore no transport of fluid through the valve plate 20, rather fluid is moved only on the flange side.

If the pistons 16, 16' move, as is shown in FIG. 3b, in the other direction, then the valve plate 20 is located in a second angular position such that fluid previously sucked into the chamber 23' is now pushed through the cylinder opening 32 via the cavity 22' and the channel 24' through the passage 34 into the outlet port 13. At the same time new fluid is sucked from the inlet port 12 through the passage 35 via the channel 24 into the cavity 22 and from there through the cylinder opening 31 into the chamber 23. Also a nearly uninterrupted pumping can be achieved, wherein in this angular position an exclusive transport of fluid occurs through the valve plate.

Figure 4A:
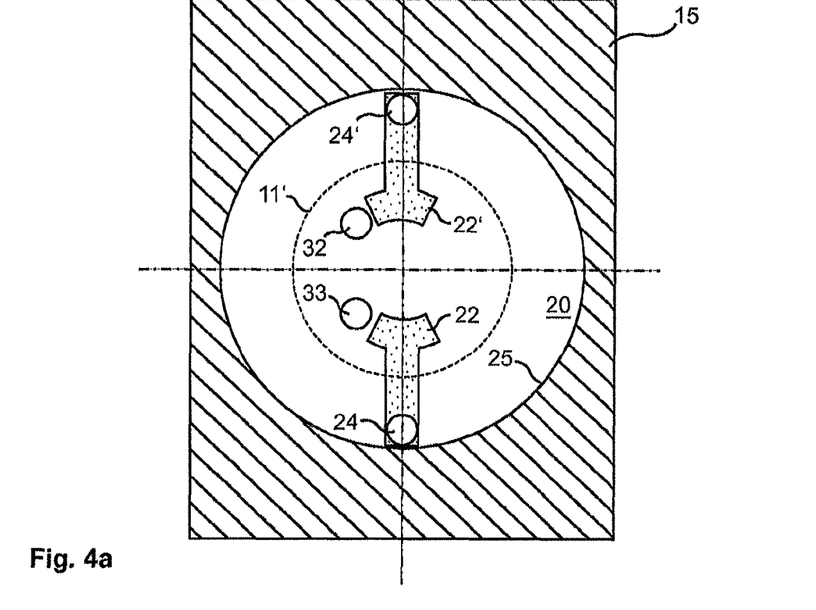
FIG. 4a shows a schematic view of a first flange having a valve plate for a multi-piston pump having one-sided inlet and outlet port.
Figure 4B:
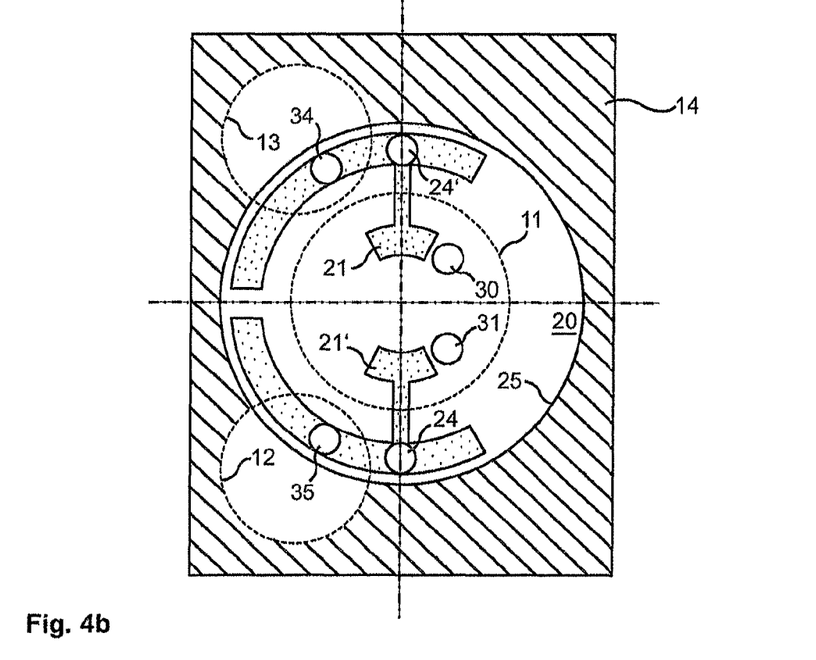
FIG. 4b shows a schematic view of a second flange having a valve plate for a multi-piston pump with one-sided inlet and outlet port.

The principal construction of a valve plate 20 is shown in FIGS. 4a and 4b, which is an embodiment of a multi-piston pump according to FIGS. 2a and 2b and two respective cavities of the same type are provided on each side of the valve plate 20. Viewing direction in the two drawings is from the cylinder 11' outwards to the flanges 14, 15 along the cylinder axis 26. Cylinders 11, 11', ports 12, 13 and the valve plate periphery 25 are shown as they are seen from this viewing direction. The projection of the cylinder 11' on the flange 15 in FIG. 4a is seen as a broken line. The circles 32 and 33 represent the cylinder openings of this cylinder 11' and are executed as breakthroughs in the flange 15. The valve plate functions are realized by the cavities 22, 22' as well as by two passage channels 24, 24' to the opposite-lying valve plate side. Since the cylinder openings 32 and 33 in the valve plate position shown are separated from the cavities 22, 22', the cylinder 11' is completely blocked.

FIG. 4b shows the flange 14 with the projections of the cylinder 11, as well as the inlet and outlet ports 12, 13 of a pump, wherein these projections are shown again as broken circles. The cylinder openings 30 and 31 of the cylinder 11 are executed as breakthroughs in the flange 14, while the passages in the ports 12, 13 are indicated by the circles 34 and 35. Depending on function, the valve plate side comprises further and clearly longer cavities 21 and 21', since connections to the inlet and outlet ports 12, 13 via the passages 34, 35 in the flange 14 must be made. The passages 34, 35 are executed as flange breakthroughs similarly to the openings 30, 31 to the cylinder 11. In the sketched valve plate position, the cylinder 11 is also blocked by the valve plate 20, and is completely separated from the inlet and outlet port 12, 13.

Figure 5A:
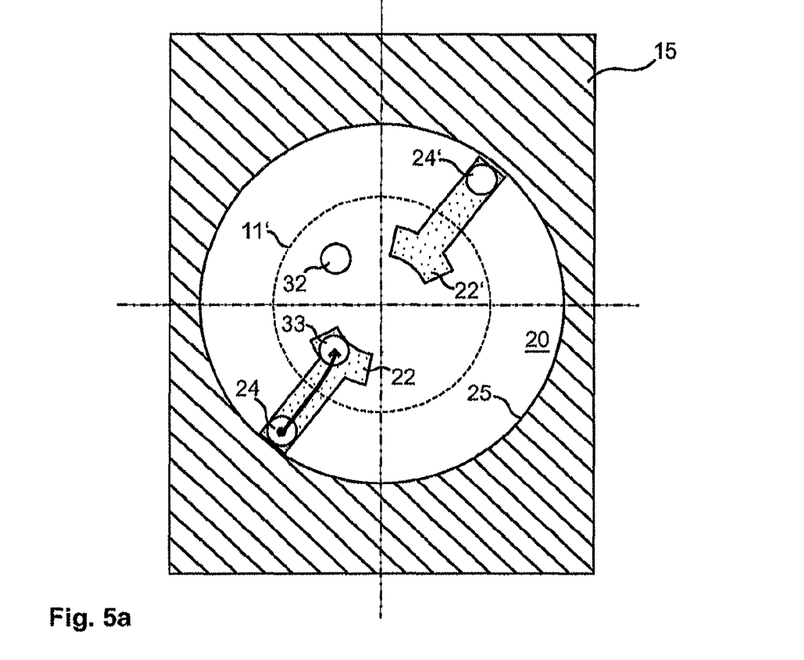
FIG. 5a shows the functional mechanism of a valve plate for a multi-piston pump having inlet and outlet port on one side for a first cylinder, during the suction process.

The functional mechanism of the valve plate 20 is shown in FIGS. 5a to 6b, wherein the valve plate has been moved from the position of FIGS. 4a and 4b. The illustrations are applied analogously to FIGS. 4a and 4b on the two flanges 14 and 15. In FIG. 5a the cylinder 11' sucks in and at the same time the cylinder 11 pushes out, as is shown in FIG. 5b. Conversely cylinder 11' in FIG. 6a pushes out and cylinder 11 in FIG. 6 sucks in.

The clockwise rotation of the valve plate 20 shown in FIG. 5a results in the cavity 22 reaching the inlet opening 33 of the cylinder 11', while the opposite-lying cavity 22' moves further away from the cylinder opening 32. The cavities on the other side of the valve plate also correspondingly turn, wherein the cavity 21 on the other valve plate side is reached through the passage channel 24. This cavity 21 represents a connection to the inlet port 12 via the passage 35 such that the cylinder 11' can suck in the fluid from the inlet port 12. This fluid path is shown in FIGS. 5a and 5b with arrows.

Figure 5B:
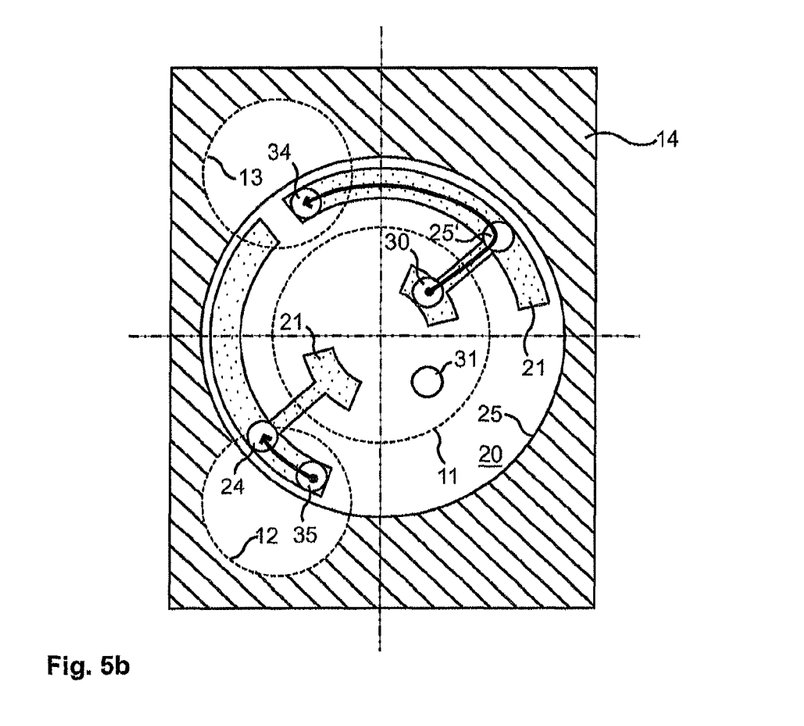
FIG. 5b shows the functional mechanism of a valve plate for a multi-piston pump according to FIG. 5a for a second cylinder, during the ejection process.

At the same time the opening 30 of the cylinder 11 in FIG. 5b is connected to the outlet port 13 via the cavity 21' and the passage 34. Thus cylinder 11 pushes the fluid out via the outlet port 13, which is also shown by an arrow in FIG. 5b and corresponds as a whole to the situation in FIG. 2a.

Figure 6A:
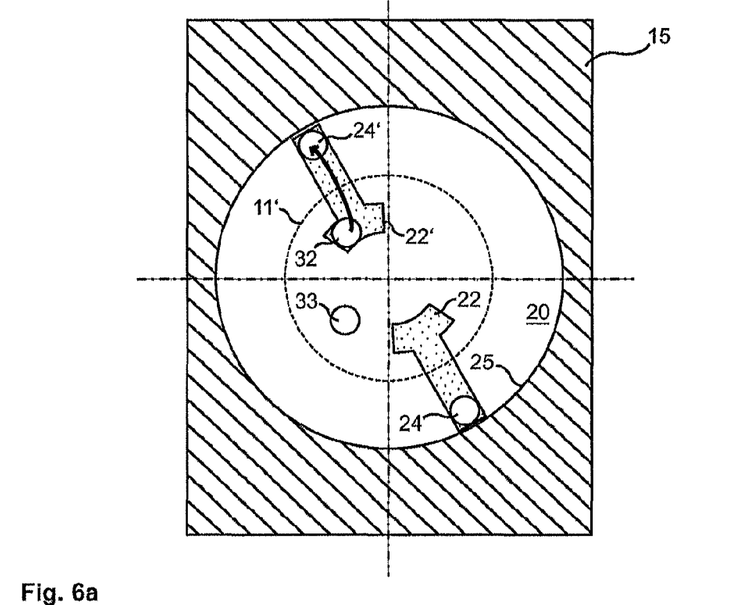
FIG. 6a shows the functional mechanism of a valve plate according to FIG. 5a for the first cylinder, during the ejection process.
Figure 6B:
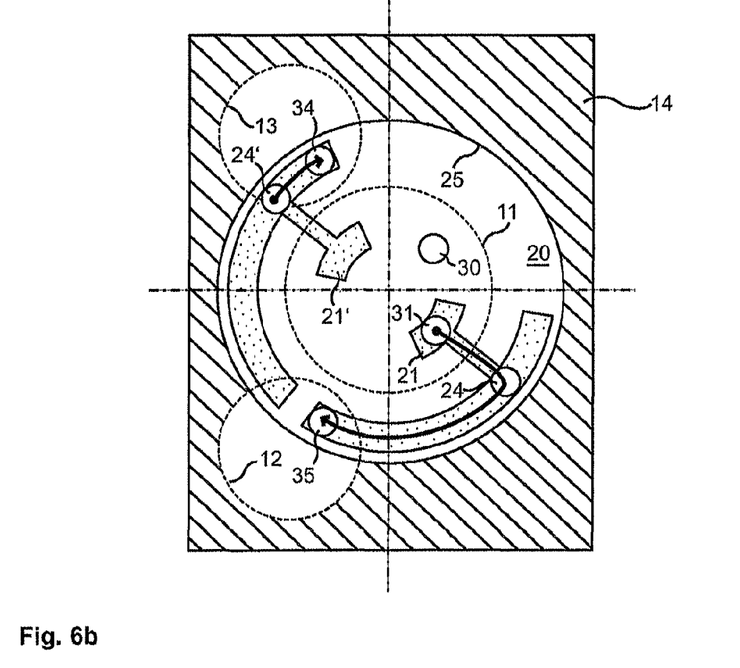
FIG. 6b shows the functional mechanism of a valve plate according to FIG. 5b for the second cylinder, during the suction process.

In FIGS. 6a and 6b, the valve plate 20 is rotated further clockwise or backwards, i.e. counter-clockwise. In the illustration of FIG. 6a the cavity 22' is thereby now connected to the opening 32 of the cylinder 11'. The previously sucked-in fluid passes from the cylinder 11' via the channel 24' to the other side of the valve plate 20 and passes from there via the passage 34 in the flange 14 to the outlet port 13. At the same time the cavity 21 connects the inlet port 12 to the opening 31 of the cylinder 11 via the passage 35 in the flange 14. Thus the sucking-in by the piston 16 in cylinder 11 is ensured, which corresponds as a whole to the situation in FIG. 2b.

The selected geometric arrangement of the cylinder openings 30, 31, 32, 33, as well as the embodiments of the cavities 21, 21',22, 22' and the passage channels 24, 24' determine the angle-dependent valve function and in particular the dead time, i.e. the angular region in which the valve function is being switched from sucking in to pushing out and within which no piston movement is allowed to take place.

In the embodiment examples of FIGS. 1a to 3b a sensor component 40, 41 is introduced to the inlet and outlet ports 12, 13 respectively, as is explained in more detail with reference to FIGS. 7 to 12. Thereby the relevant region in an inlet port 12 having a sensor component 40 is exemplary shown in the figures.

Figure 7:
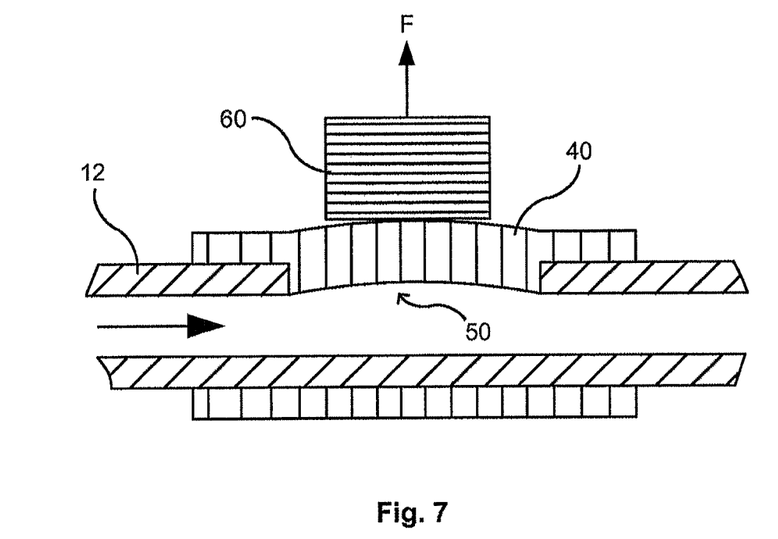
FIG. 7 shows a longitudinal section through a port having externally lying sensor component.

The longitudinal section through a port 12 shown in FIG. 7 shows an externally lying sensor component 40 which surrounds the port 12 in the region of a recess 50 with form-locking fit. A sealed connection is achieved here between the port 12 and the tubular sensor component 40. The sensor component 40 may be formed on its inner side such that it is partially inserted into the recess 50, as is shown in FIG. 7. The occlusion sensor may advantageously be made in a two-component process by injection molding, wherein the sensor component 40 is applied as a second process step after the manufacture of a tubular port 12 from a hard component. As a material for the hard component, a hard plastic may be selected, while the sensor component is composed of an elastic and pressure sensitive material such as an elastomer.

Figure 8:
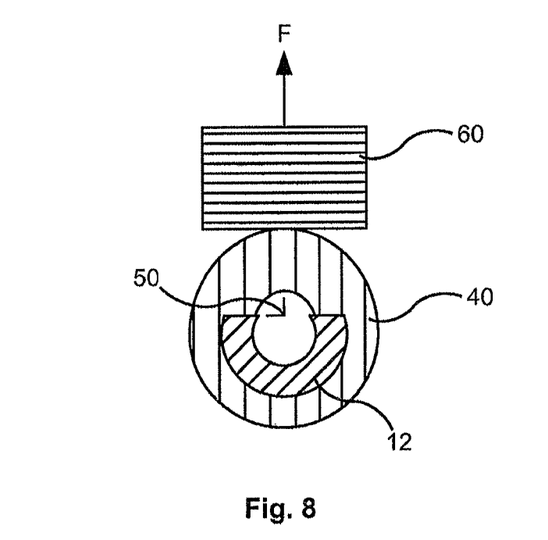
FIG. 8 shows a cross-section through a port according to FIG. 7.

The recess 50 may have an arbitrary cross-section, wherein round cross-sections have proved to be advantageous for an even force distribution. Furthermore the size of the recess 50 should be appropriately chosen. In FIG. 8 for example a cross-section through the middle of the longitudinal section of FIG. 7 is shown, whereby the recess 50 has been selected to be very deep and reaches approximately to the centerline of the port 12.

A force sensor 60 can then reach through the recess 50 so as to establish contact in this region with the outer side of the sensor component 40 and to mechanically detect the deformation of the membrane 20. This may take pike for example via a plunger 60 which bears on the sensor component. When the internal pressure in the port 12 increases due to an occlusion, the sensor component 40 bends outwardly, which can be detected by the plunger 60. When the pressure in the port 12 decreases due to an occlusion, the curvature of the sensor component 41 reduces, which also can be detected by the plunger 60.

Figure 9:
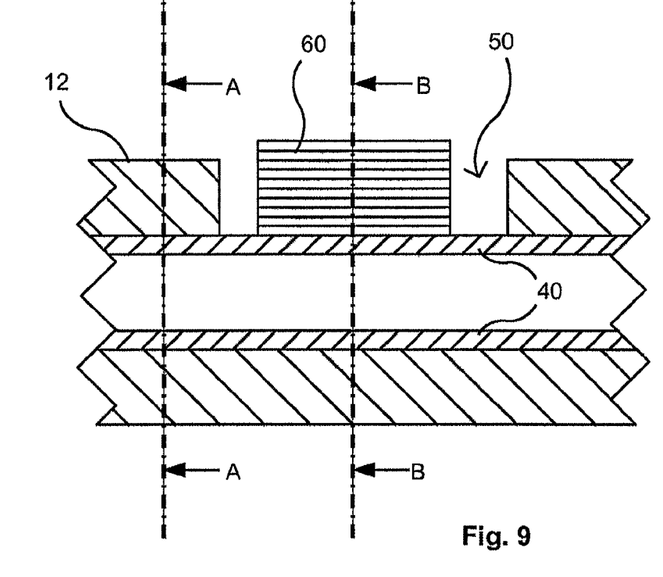
FIG. 9 shows a longitudinal section through a port having a first exemplary embodiment of an inwardly lying sensor component.

FIG. 9 shows a second exemplary embodiment of the invention, whereby a tubular sensor component 40 is attached inside a port 12 and thus tightly covers a recess 50 from inside. Also this occlusion sensor may be made here in a two-component process by injection molding in the form of a continuous inner tube as soft component, while the associated inlet or outlet port is made in an integral and non-disassemblable way, as an overlying support pipe or supporting skeleton, as hard component. Thereby the inner surface of the port 12 may be configured such that it keeps the tube 40 in its position and prevents an axial sliding (not shown).

Figure 10:
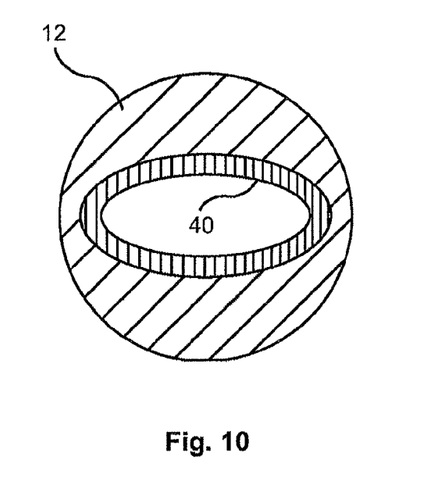
FIG. 10 shows a first cross-section through a port according to FIG. 9.
Figure 11:
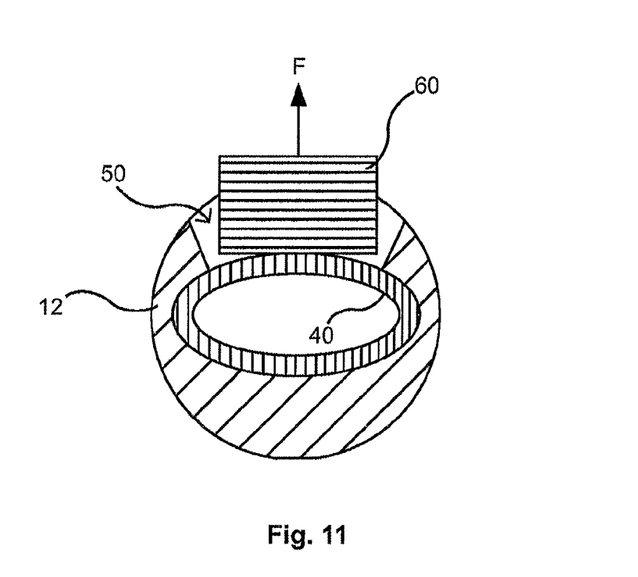
FIG. 11 shows a second cross-section through a port according to FIG. 9.

FIG. 10 Shows a first a cross-section through such a port along line A-A, whereby it can be seen that the sensor component 40 has an elliptical cross-section. The inner wall of the port 12 is suitably formed in order to be able to accommodate the sensor component 40 with form-locking fit. A second cross-section along the line B-B is depicted in FIG. 11 and shows also the plunger 60 which contacts the outer surface of the sensor component through the recess 50.

Figure 12:
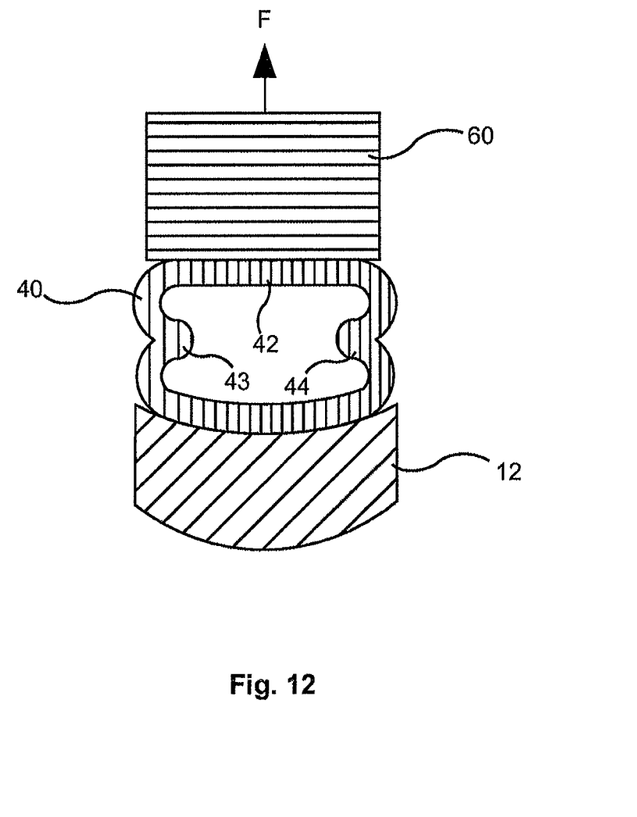
FIG. 12 shows a cross-section through a port having a second exemplary embodiment of an inwardly lying sensor component.

In order to prevent to the greatest possible extent internal stresses of the sensor component 40, this may also be configured as a specially formed measurement membrane, as is shown for example in FIG. 12. The measurement membrane 40 here comprises two opposite-lying membrane sides 43 and 44, which are kinked inwards. The membrane top side 42, which connects the two membrane sides 43, 44, is executed in a straight manner and is in contact with the plunger 60. The membrane top side 42 is no longer changed by the internal stress, which results in a linear force characteristic: force=internal pressure×membrane surface area.

The cross-section of the sensor component 40 is thus individually formed and contains at least one of the following functional components:
- A straight or approximately straight line which determines the geometry of the membrane required for measurement purposes.
- A straight or curved line opposite the membrane, which performs a support function of the soft component with respect to the tubular or skeletal hard component.
- A geometry for the realization of a spring function on the two sides of the soft component, so that a preload can be set up, which is necessary for the measurement of pressures below ambient atmospheric pressure. In addition the spring function is necessary so that the membrane can remove itself from its opposite-lying support surface upon an increasing inner pressure.

The inner surface of the port 12 may then be suitably executed such that the measurement membrane 40 bears on it with form-locking fit and does not extend in undesired directions, e.g. to the side, upon a pressure rise. Also this special shape of the port 12 may be provided only in the region of the occlusion sensor, whereby costly forms within the entire port can be avoided.

The hard component which surrounds the plunger 60 preferably comprises a planar surface, which lies approximately underneath the plunger's upper edge. This surface serves as an abutment surface when the plunger is pushed against another surface. The plunger can then be pushed only by the amount of its overhang, whereby a constant preload for the pressure sensor is created.

In the exemplary embodiments shown in FIGS. 7 to 12, the recess 50 and thus the plunger 60 is located always at the top in the port 12, but also other arrangements may be chosen.

Figure 13:
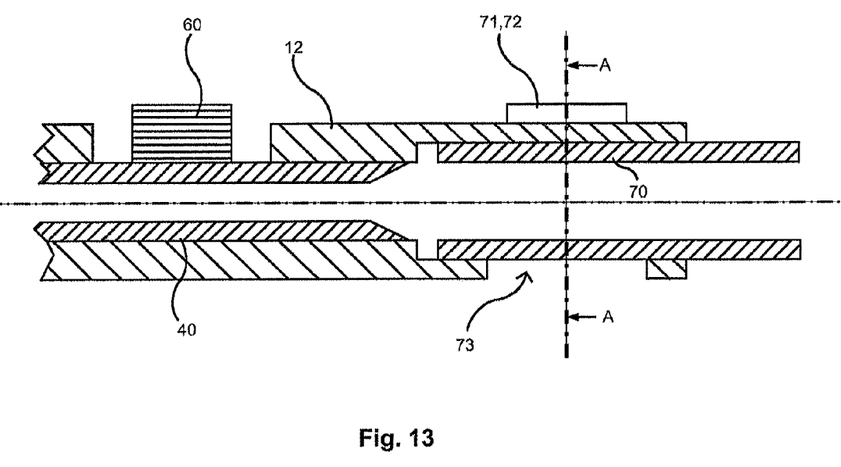
FIG. 13 shows a longitudinal section through a port with inwardly lying sensor component and ultrasound sensor.
Figure 14:
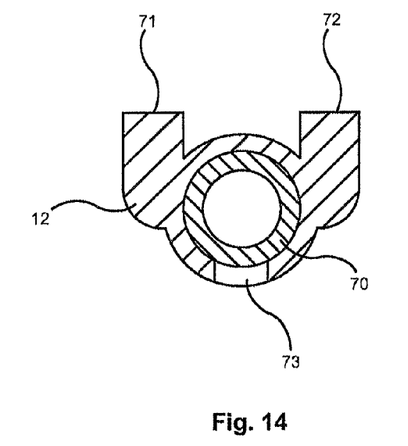
FIG. 14 shows a cross-section through a port with the ultrasound sensor according to FIG. 13.

An optional ultrasound sensor for the piston pump 10 according to aspects of the invention is shown, together with an inwardly lying sensor component, 40 in FIG. 13, which renders the additional manual introduction of a tube into special holders superfluous. With this ultrasound sensor, air bubbles in the infusion tube system can be recognized, wherein also this ultrasound sensor may be attached inside the inlet and/or outlet port 12, 13. In FIG. 13 the ultrasound sensor is shown exemplarily in the inlet port 12. For this purpose, this port 12 is suitably widened on the inside at its end such that a flexible tube 70 can be introduced there and fixed by gluing for example. The coupling and decoupling of the ultrasound occurs at two opposite-lying surfaces 71, 72 which preferably may be executed to be flat, as is shown in FIG. 14 in cross-section along line A-A. The two surfaces 71, 72 thereby lie in one plane. However other form-locking connections, e.g. with a cone, are also conceivable. A recess 73 in the inlet port 12 is located opposite the flat surfaces 71, 72.

As with the occlusion sensor, the mechanical components for the air bubble detection preferably also form an integral component of the tubular ports and cannot be disassembled non-destructively. Comparable adaptations of the pump apparatus for supporting the sensor are also possible, for example to allow alternative optical air bubble recognition methods or to allow the formation of defined interfaces for a measurement of temperature.

The coupling and decoupling surfaces for the ultrasound as well as the abutment surface for the occlusion sensor preferably form a plane, whereby the interface to the associated electronic sensors also forms a plane which can be located for example in a medical device. Through this means, requirements for a good and simple cleanability can be advantageously implemented.

The invention claimed is:

1. A piston pump for pumping a fluid, comprising:
   at least one cylinder, each cylinder having a piston movable inside the cylinder along the longitudinal axis of the cylinder, wherein each cylinder has an end face;
   at least one mounting flange having a cylinder-side and a respective cylinder situated on the cylinder-side, and the at least one mounting flange also having a plate-side opposite the cylinder-side, wherein at least one cylinder opening extends between the cylinder-side and the plate-side, the at least one mounting flange and its respective cylinder defining at least one chamber having a volume that changes when the piston in the respective cylinder is moved;
   an inlet port for supplying and an outlet port for draining the fluid attached to the at least one mounting flange, at least one of the inlet port or the outlet port including a recess, wherein the inlet port and the outlet port each are arranged on the cylinder-side of the at least one mounting flange;
   a rotatable valve plate arranged on the plate-side of the at least one mounting flange, the rotatable valve plate configured to bear on the respective mounting flange and attached to the at least one mounting flange,
      wherein the at least one mounting flange has at least one passage for each of the inlet port and the outlet port through which passage the fluid can flow between the inlet port or outlet port and the plate-side of the at least one mounting flange, and wherein the valve plate rotates between two angular positions and has at least one surface, the at least one surface having at least one recessed cavity for fluid-transport, wherein upon rotation of the valve plate between the two angular positions, in each of the two angular positions the at least one cylinder opening is connected to the at least one passage for fluid flow with the inlet port or the outlet port;

an occlusion sensor comprising a sensor component, wherein the occlusion sensor is integrated into the inlet port or the outlet port, and wherein the sensor component tightly covers the recess, the sensor component is composed of an elastic pressure sensitive material, and a material comprising the inlet port and the outlet port is harder than the elastic pressure sensitive material;

a force sensor extending into the recess such that the force sensor contacts a surface of the sensor component, and wherein the force sensor is configured to measure pressure-induced changes of the sensor component in the region of the recess; and an ultrasound sensor integrated into at least one of the inlet port or the outlet port, and configured to detect air bubbles in the respective inlet port or outlet port.

2. The piston pump according to claim 1, further comprising a tube inserted into at least one of the inlet port or the outlet port with form-locking fit, through which fluid is supplied to the inlet port or discharged from the outlet port.

3. The piston pump according to claim 2, wherein surfaces for the coupling and decoupling of the ultrasound sensor are provided in the region of the tube on two sides of the respective inlet port or outlet port.

4. The piston pump according to claim 3, wherein the at least one of the inlet port or the outlet port is formed such that the surfaces lie in a plane.

5. The piston pump according to claim 4, wherein the at least one of the inlet port or the outlet port comprises at least one further recess.

6. The piston pump according to claim 1, wherein the inlet port and the outlet port each have a longitudinal axis that is parallel to the longitudinal axis of the at least one cylinder.

7. The piston pump according to claim 1, wherein the ultrasound sensor cannot be non-destructively disassembled.

8. A piston pump for pumping a fluid, comprising:
at least one cylinder, each cylinder having a piston movable inside the cylinder along the longitudinal axis of the cylinder, wherein each cylinder has an end face;
at least one mounting flange, each mounting flange having a cylinder-side, a plate side opposite the cylinder side, and a respective one of the at least one cylinder situated on the cylinder-side, wherein at least one cylinder opening extends between the cylinder-side and the plate-side, the at least one mounting flange and the respective cylinder defining a respective chamber having a volume that changes when the piston in the respective cylinder is moved;

an inlet port for supplying and an outlet port for draining the fluid, the inlet port and the outlet port attached to the at least one mounting flange, wherein the inlet port and the outlet port are each arranged on the cylinder-side of the at least one mounting flange;

a rotatable valve plate arranged on the plate-side of a respective one of the at least one mounting flange, the rotatable valve plate attached to the respective mounting flange,
wherein the at least one mounting flange has at least one passage for each of the inlet port and the outlet port through which the fluid can flow between the inlet port or outlet port and the plate-side of the at least one mounting flange, and
wherein the rotatable valve plate rotates between two angular positions and has at least one surface, the at least one surface having at least one recessed cavity for fluid transport, wherein in each of the two angular positions the at least one cylinder opening is connected to the at least one passage for fluid flow with the inlet port or the outlet port; and an ultrasound sensor integrated into at least one of the inlet port or the outlet port, and configured to detect air bubbles in the at least one inlet port or outlet port.

9. The piston pump according to claim 8, further comprising a tube inserted into at least one of the inlet port or the outlet port with form-locking fit, through which fluid is supplied to the inlet port or discharged from the outlet port.

10. The piston pump according to claim 9, wherein surfaces for the coupling and decoupling of the ultrasound sensor are provided in the region of the tube on two sides of the respective inlet port or outlet port.

11. The piston pump according to claim 10, wherein the at least one of the inlet port or the outlet port is formed such that the surfaces lie in a plane.

12. The piston pump according to claim 8, wherein the inlet port and the outlet port each have a longitudinal axis that is parallel to the longitudinal axis of the at least one cylinder.

13. The piston pump according to claim 8, wherein the ultrasound sensor cannot be non-destructively disassembled.

* * * * *